(12) United States Patent
Kohut et al.

(10) Patent No.: US 8,390,624 B2
(45) Date of Patent: Mar. 5, 2013

(54) INTERRELATED GRAPHICAL METHOD FOR DISPLAYING BLOOD PRESSURE DATA

(75) Inventors: Michael Lambert Kohut, Chico, CA (US); Richard Bruce Bordenkircher, Meridan, ID (US)

(73) Assignee: DataDancer Medical Systems, Chico, CA (US)

( * ) Notice: Subject to any disclaimer, the term of this patent is extended or adjusted under 35 U.S.C. 154(b) by 214 days.

(21) Appl. No.: 13/065,416

(22) Filed: Mar. 21, 2011

(65) Prior Publication Data

US 2011/0234597 A1   Sep. 29, 2011

Related U.S. Application Data

(60) Provisional application No. 61/341,235, filed on Mar. 29, 2010.

(51) Int. Cl.
*G06T 11/20* (2006.01)
*A61B 5/02* (2006.01)
*A61B 5/00* (2006.01)

(52) U.S. Cl. ......... 345/440; 600/485; 600/504; 600/301

(58) Field of Classification Search .................. None
See application file for complete search history.

(56) References Cited

U.S. PATENT DOCUMENTS

| | | | |
|---|---|---|---|
| 2008/0281168 A1* | 11/2008 | Gibson et al. | 600/301 |
| 2009/0131805 A1* | 5/2009 | O'Brien et al. | 600/485 |
| 2010/0234742 A1* | 9/2010 | Lin | 600/490 |

OTHER PUBLICATIONS

"Blood Pressure Chart" http://www.lifemana.com/blood-pressure-chart.html. Archived on Oct. 7, 2008. Retrieved on Nov. 5, 2012 from <http://web.archive.org/web/20081007223809/http://www.lifemana.com/blood-pressure-chart.html>.*

"Blood Pressure Tracking" http://raywinstead.com/bp/. Archived on Apr. 18, 2009. Retrieved on Dec. 11, 2012 from <http://web.archive.org/web/20090418022225/http://raywinstead.com/bp/>.*

* cited by examiner

*Primary Examiner* — Kee M Tung
*Assistant Examiner* — Zhengxi Liu

(57) ABSTRACT

A graphical method of displaying interrelated blood pressure data that effectively communicates patient or group performance within or between discrete datasets. The graphical method displays Systolic Pressure (SP), Diastolic Pressure (DP), Pulse Pressure (PP), Mean Arterial Pressure (MAP) and the Classification of Blood Pressure as related to a single data point or a plurality of data points from a discrete dataset. Multiple datasets can be simultaneously displayed for comparison purposes allowing patients, physicians or scientists to understand the relative differences in dataset performance across a series of datasets.

4 Claims, 2 Drawing Sheets

INTERRELATED GRAPHICAL METHOD FOR DISPLAYING BLOOD PRESSURE DATA

CROSS-REFERENCE TO RELATED APPLICATIONS

This application claims the benefit of Provisional Patent Application No. 61/341,235 filed 2010 Mar. 29 by the present inventors.

STATEMENT REGARDING FEDERALLY SPONSORED RESEARCH OR DEVELOPMENT

Not Applicable

BACKGROUND OF THE INVENTION

No applicable prior art could be found specifically relating to our invention. Our invention is an interrelated, multi-parameter, graphical presentation of blood pressure (BP) data. BP data is usually obtained from medical instrumentation, personal blood pressure monitors or human operated sphygmomanometer. Primary BP data parameters such as Systolic Pressure (SP), Diastolic Pressure (DP) and Pulse Rate (PR) are regularly measured directly by medical professionals in the pursuit of patient health or research. These BP parameters were sometimes plotted manually, before the advent of computers, as an aid to increased understanding of the data. However, with the advancement of technology, these parameters are now displayed by computer software for instantaneously viewing. Secondary BP data parameters such as Pulse Pressure (PP), Mean Arterial Pressure (MAP) and the Classification of BP (CBP), derived from primary parameter (SP & DP) calculations, are also computer displayed to aid in the advanced understanding of BP data. These primary and secondary BP data parameters are usually plotted graphically, singularly or in related combinations, allowing patients, physicians or scientists to observe BP data trends, the results of statistical analyses and BP parameter relationships, as they pursue their individual endeavors. Presently, it requires a plurality of graphs to comprehensively display a hypertension patient's BP performance within a single treatment or across multiple trial treatments. Our invention displays the following primary and secondary BP data parameters in a single, interrelated graph: SP, DP, PP, MAP and CBP. Therefore, our invention significantly improves the comprehensive understanding of BP data through an innovative and efficient graphic presentation, aiding in patient treatment and research.

SUMMARY OF THE INVENTION—OBJECT

The object of our invention is to incorporate the primary blood pressure (BP) parameters, Systolic Pressure (SP) and Diastolic Pressure (DP), with the secondary blood pressure parameters, Pulse Pressure (PP), Mean Arterial Pressure (MAP) and the Classification of Blood Pressure (CBP), into a single graphical display to effectively communicate patent performance across multiple BP datasets or within a single BP dataset. BP datasets may be different trial treatments prescribed by a physician, increments of time within a specific treatment, self imposed life style changes such as diet and exercise, or group dynamics in a research environment.

SUMMARY OF THE INVENTION—ADVANTAGES

The advantages of our invention are listed below. However, there may be other advantages, unknown at this time, due to the versatility and adaptability of our invention.

1) Provides a comprehensive and interrelated graphical presentation of blood pressure (BP) performance by incorporating the following parameters into a single scatter graph: Systolic Pressure (SP), Diastolic Pressure (DP), Pulse Pressure (PP), Mean Arterial Pressure (MAP), Classification of Blood Pressure (CBP) and an Optimal Blood Pressure Area.
2) Allows users to simultaneously display different blood pressure datasets, obtained under different conditions, to directly observe and compare blood pressure dataset performance graphically.
3) Enables physicians to better understand patient blood pressure performance within and across a plurality of trial treatments, therefore, aiding in the efficient selection of the optimum patient treatment.
4) Allows patients to easily observe and compare their personal blood pressure performance within and across a plurality of trial treatments, maintaining patient involvement in the process of improving their cardiovascular health.

DRAWING DESCRIPTIONS

From this point forward, the invention will be referred to as the "bp Quad Plot".

FIG. 1: by Quad Plot—Without Displayed Data
FIG. 2: by Quad Plot—With Three (3) Sets of Data Displayed

DRAWING REFERENCE NUMERALS 1 by Quad Plot
2 Systolic Pressure (SP) Axis
3 Systolic Pressure (SP) Reference Grid Lines
4 Diastolic Pressure (DP) Axis
5 Diastolic Pressure (DP) Reference Grid Lines
6 Pulse Pressure (PP) Reference Grid Lines
7 Pulse Pressure (PP) Zero Reference Grid Line
8 Mean Arterial Pressure (MAP) Reference Grid Lines
9 Classification of Blood Pressure (CBP) Categories
10 Stage 2 Classification of Blood Pressure (CBP) Reference Lines
11 Stage 1 Classification of Blood Pressure (CBP) Reference Lines
12 Pre Hypertension Classification of Blood Pressure (CBP) Reference Lines
13 Normal Classification of Blood Pressure (CBP) Reference Lines
14 Low Normal Classification of Blood Pressure (CBP) Area
15 Optimal Blood Pressure Area
16 Data Set 1
17 Data Set 2
18 Data Set 3
19 Mean Arterial Pressure (MAP) labels
20 Pulse Pressure (PP) labels

DESCRIPTION OF FIGURES

FIG. 1 displays the by Quad Plot without plotted blood pressure data to better describe the graphical components of the invention.
FIG. 1-1 Identifies the invention as the by Quad Plot.
FIG. 1-2 Identifies the Systolic Pressure (SP) Axis with major and minor magnitude marks.

FIG. 1-3 Identifies a Systolic Pressure (SP) Reference Grid Line as associated with the major magnitude marks on the Systolic Pressure (SP) axis.

FIG. 1-4 Identifies the Diastolic Pressure (DP) Axis with major magnitude marks.

FIG. 1-5 Identifies a Diastolic Pressure (DP) Reference Grid Line as associated with the major magnitude marks on the Diastolic Pressure (DP) axis.

FIG. 1-6 Identifies a Pulse Pressure (PP) Reference Grid Line as associated with the major magnitude marks on the Systolic Pressure (SP) axis and PP magnitude labels.

FIG. 1-7 Identifies the Pulse Pressure (PP) Zero Reference Grid Line.

FIG. 1-8 Identifies a Mean Arterial Pressure (MAP) Reference Grid Line as associated with a plurality of MAP magnitude labels.

FIG. 1-9 Identifies one in the series of Classification of Blood Pressure (CBP) category labels.

FIG. 1-10 Identifies the Stage 2 CBP Reference Lines. All data points plotted on or above these lines in magnitude are classified as Stage 2 Hypertension.

FIG. 1-11 Identifies the Stage 1 CBP Reference Lines. All data points plotted on or above these lines and below the Stage 2 CBP lines in magnitude are classified as Stage 1 Hypertension.

FIG. 1-12 Identifies the Pre Hypertension CBP Reference Lines. All data points plotted on or above these lines and below the Stage 1 CBP lines in magnitude are classified as Pre Hypertension.

FIG. 1-13 Identifies the Normal CBP Reference Lines. All data points plotted on or above these lines and below the Pre Hypertension CBP lines in magnitude are classified as Normal.

FIG. 1.14 Identifies the Low Normal CBP area which is located below the Normal CBP lines in magnitude.

FIG. 1-15 Identifies the Optimal Blood Pressure Area (OBPA) defined by the Normal CBP components SP and DP, optimal PP limits of normality and optimal MAP limits or normality.

FIG. 1-19 Identifies one in a series of Mean Arterial Pressure (MAP) magnitude labels.

FIG. 1-20 Identifies one in a series of Pulse Pressure (PP) magnitude labels.

FIG. 2:

FIG. 2 shows the by Quad Plot with three (3) different blood pressure datasets to demonstrate how a plurality of blood pressure datasets can be simultaneously displayed.

FIG. 2-1 Identifies the invention as the by Quad Plot.

FIG. 2-16 Identifies Data Set 1 displayed as opaque dots.

FIG. 2-17 Identifies Data Set 2 displayed as plus symbols.

FIG. 2-18 Identifies Data Set 3 displayed as white squares.

DETAILED DESCRIPTION OF THE INVENTION

Figure 1:
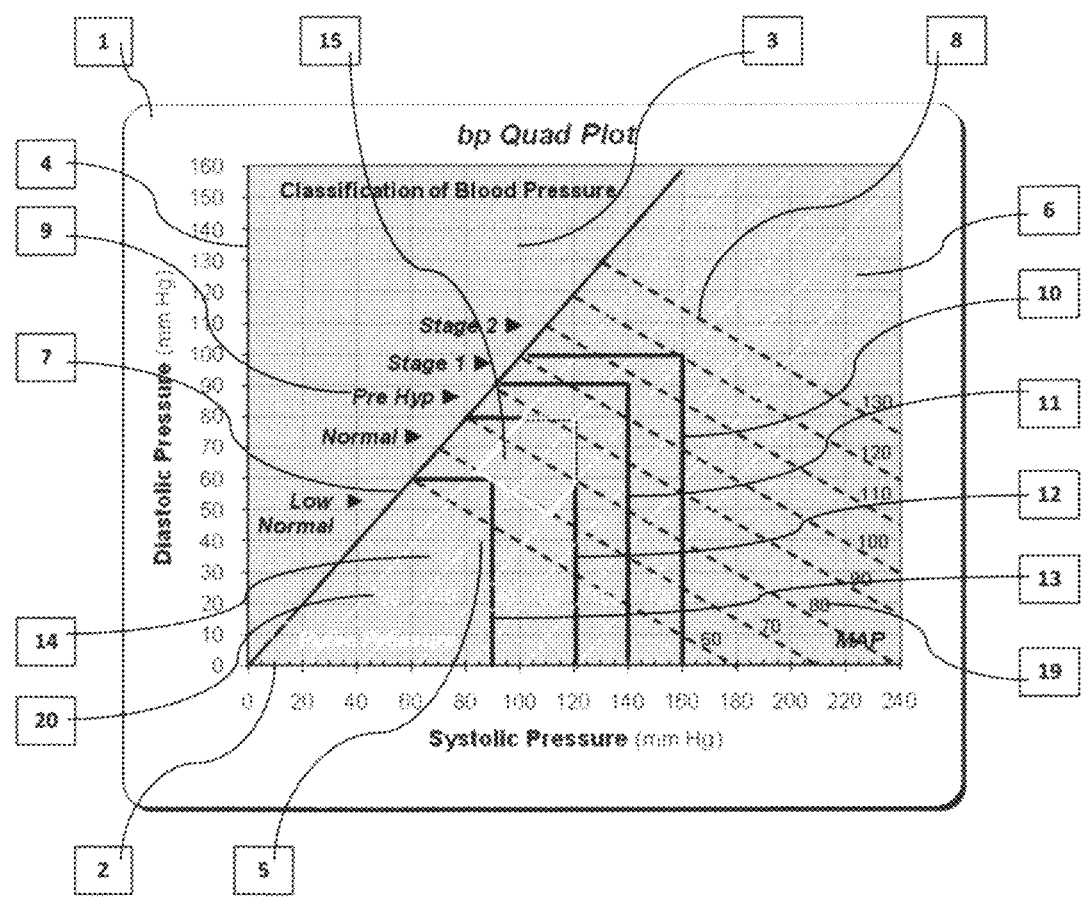
FIG. 1.
Figure 2:
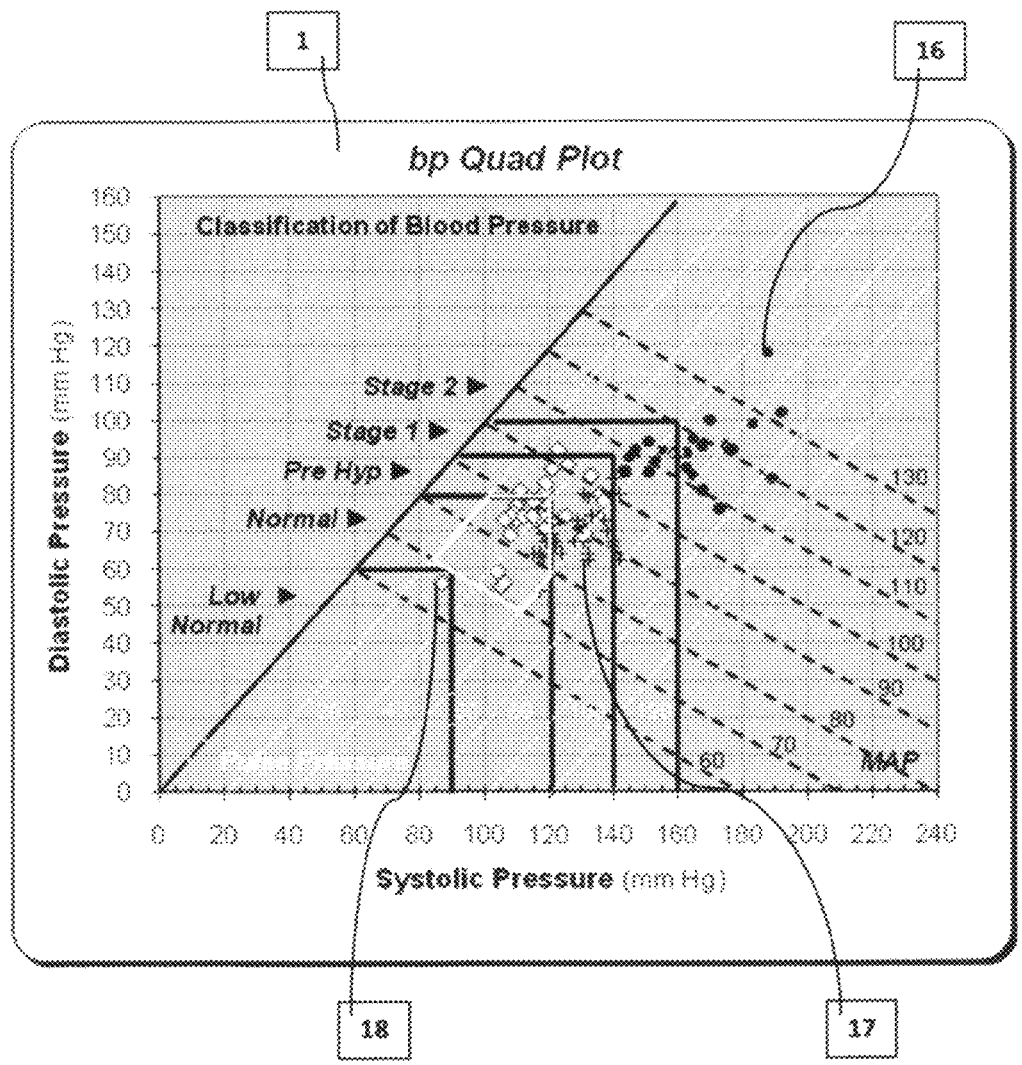

One example of an embodiment of the invention would incorporate the by Quad Plot (FIGS. 1.1 and 2-1) graph into a blood pressure (BP) software program designed to incrementally log and track patient BP measurement results across multiple trial treatments. The BP results from each trial treatment would be entered into separate logs within the software program and designated appropriately. The invention would display the blood pressure data from each log in a different color and/or geometric shape, thus allowing multiple trial treatments from different logs to be simultaneously displayed, recognized and assessed with respect to patient BP performance (FIGS. 2-16, 2-17 and 2-18).

In this by Quad Plot example, the results of a single blood pressure (BP) measurement set are entered into a specific log reserved for data associated with a specific trial treatment. The data from the log is then plotted as a function of Systolic Pressure (SP) (FIG. 1-2) and Diastolic Pressure (DP) (FIG. 1-4) resulting in a single plotted BP data point. Multiple blood pressure measurement sets, and the corresponding plotted BP data points, create a plurality of BP data points within the by Quad Plot graph. The plurality of BP data points (FIG. 2-16) plotted from a specific log represents the performance of a single trial treatment with respect to the following by Quad Plot parameters: Systolic Pressure (SP), Diastolic Pressure DP, Pulse Pressure (PP) (FIG. 1-6), Mean Arterial Pressure (MAP) (FIG. 1-8), Classifications of Blood Pressure (CBP) (FIG. 1-9) and Optimal Blood Pressure Area (OBPA) (FIG. 1-15). Additionally, the visual scatter of the plotted data points from different trial treatments, present the user with a visual comparison of data imprecision across said trail treatments.

The Pulse Pressure (PP) Zero Reference Grid Line (FIG. 1-7) is created by connecting a series of BP data points within the by Quad Plot where SP is equal to DP in parameter magnitude. Since PP=SP−DP mathematically, the PP of all such data points is equal to zero. By varying the magnitudes of SP and DP and subsequently connecting all the resulting PP zero data points with a straight line establishes the PP Zero Reference Grid Line. Using the PP Zero Reference Grid Line as a reference, other PP reference gridlines (FIG. 1-6), parallel to the PP Zero Reference Grid Line (FIG. 1-7), can be created in other PP magnitudes. Using the Systolic Pressure (SP) axis as a PP magnitude reference, other PP reference gridlines can be appropriately positioned. PP labels are also utilized for easy reference (FIG. 1-20).

The Mean Arterial Pressure (MAP) Reference Grid Lines (FIG. 1-8) are created by solving the MAP equation MAP=DP+⅓(SP−DP) in order to plot two data points with equivalent MAP magnitude values within the by Quad Plot graph. Once said data points are established and plotted, a straight line is drawn connecting the two points to create a MAP Reference Grid Line (FIG. 1-8). For example, if a Systolic Pressure (SP) of 180 mm Hg and a Diastolic Pressure (DP) of 0.0 mm Hg is entered into the MAP equation, this will establish the first data point on the SP axis at the 180 mm Hg point with a MAP=60 mm Hg. To establish the second data point simply select a different value for SP (100 mm Hg) and solve the MAP equation for DP using a MAP=60 mm Hg. Using SP=100 and MAP=60, the DP will equal 40.05 mm Hg. To locate the second data point corresponding to a MAP value of 60 mm Hg, plot a data point at the intersection of axis values corresponding to SP of 100 mm Hg (FIG. 1-3) and a DP of 40.05 mm Hg (FIG. 1-5). Connecting the two MAP data points with a straight line will create a MAP Reference Grid Line corresponding to 60 mm Hg. Other MAP Reference Grid Lines can be created by solving the MAP equation for other MAP values with appropriate substitutions of SP or DP values to establish corresponding data points. Since the MAP values will not correspond to either SP or DP axis values, all MAP Reference Grid Line should be appropriately labeled (FIG. 1-19).

The Classification of Blood Pressure (CBP) (FIG. 1-9) is an accepted system of categorizing the severity of the cardiovascular risk associated with high blood pressure (BP) or hypertension. The classification categories vary among different countries and medical groups, and therefore, are subject to change as new information emerges within medical science. The CBP System used within the by Quad Plot is one of several presently used in medical science throughout the world. The by Quad Plot CBP Reference Lines (FIGS. 1-10, 1-11, 1-12 and 1-13) establish categories areas (FIGS. 1.9 and 1.14) designated by the upper and lower limits of Systolic Pressure (SP) and Diastolic Pressure (DP) parameters as published by the CBP System.

The Optimal Blood Pressure Area (OBPA) (FIG. 1-15) is established by the defined parameter limits of blood pressure (BP) normality. Since the definition of "normality" or a Normal BP may be defined differently across ethnicity, populations and age, the parameter limits used to establish normality may also change. The by Quad Plot OBPA in this example was established by using the upper and lower limits of the primary and secondary BP parameters associated with normality:

The upper and lower limits of Systolic Pressure (SP) and Diastolic Pressure (DP) parameters associated with Normal BP as defined by the Classification of Blood Pressure (CBP) System utilized.

Optimal Pulse Pressure (PP) limits of normality.

Optimal Mean Arterial Pressure (MAP) limits or normality.

The advantages of the by Quad Plot in this example over other methods of displaying patient blood pressure (BP) performance can be summarized as a single graphic device that simultaneously communicates BP performance within or across multiple trial treatments. Below is a summary of the information available from the by Quad Plot example as displayed by (FIG. 2-1) by viewers not proficient in the medical art of blood pressure treatment and management. Medical doctors and other qualified viewers who understand interrelationships of the blood pressure (BP) parameters, have the opportunity to verify those relationships and make effective medical decisions to improve patient health. Additionally, patient self-monitoring BP measurement techniques are easily scrutinized via data scatter and appropriate patient education implemented as required.

Data Set 1 (FIG. 2-16): viewed as follows:
SP Range: 121 to 195 mm Hg
DP Range: 70 to 119 mm Hg
PP Range: 45 to 101 mm Hg
MAP Range: 90 to 140 mm Hg
CBP Range: Pre Hypertension to Stage 2
Optimal Area Empty
Scatter: Erratic Scatter across all parameters with extreme outliers Data Set 2 (FIG. 2-17): viewed as follows:
SP Range: 115 to 161 mm Hg
DP Range: 53 to 90 mm Hg
PP Range: 39 to 80 mm Hg
MAP Range: 75 to 115 mm Hg
CBP Range: Normal to Stage 2
Optimal Area High Normal Data
Scatter: Clustered Scatter across all parameters with outliers Data Set 3 (FIG. 2-18): viewed as follows:
SP Range: 85 to 139 mm Hg
DP Range: 52 to 91 mm Hg
PP Range: 27 to 60 mm Hg
MAP Range: 67 to 112 mm Hg
CBP Range: Low Normal to Stage 1
Optimal Area Intermittent Data
Scatter: Cluster Scatter; SP & DP low outliers

We claim:

1. An interrelated graphical method for displaying blood pressure data within a single graph that simultaneously displays parameter magnitude values of systolic pressure, diastolic pressure, pulse pressure, mean arterial pressure, and a classification of blood pressure category, from a plurality of blood pressure categories, for every graphed data point,
wherein the single graph is displayed electronically,
wherein the interrelated graphical method is executed by a computer processor,
wherein a coordinate system with reference lines is utilized to reference the parameter magnitude values of all plotted data points,
wherein systolic pressure and diastolic pressure parameter reference lines are projected as straight lines at right angles to a systolic pressure axis and a diastolic pressure axis respectively,
wherein pulse pressure parameter reference lines are projected as a series of parallel lines emanating from the systolic pressure axis at an angle equal to an angle imposed by a zero pulse pressure reference line created by connecting plotted points with a straight line that mathematically satisfy a pulse pressure equation where the difference between a systolic pressure axis magnitude value and a diastolic pressure axis magnitude value is equal to zero,
wherein a mean arterial pressure reference line is projected as a straight line emanating from the zero pulse pressure reference line at an angle imposed by connecting plotted points that mathematically satisfy a mean arterial pressure equation for several unknown axis magnitude values of diastolic pressure while maintaining a mean arterial pressure equation value as a mathematical constant and while varying systolic pressure axis magnitude values; wherein a mean arterial pressure magnitude value of the mean arterial pressure reference line corresponds to the mathematical constant utilized to calculate said plotted points that mathematically satisfy the mean arterial pressure equation,
wherein as series of mean arterial pressure reference lines are established at appropriate intervals so that all mean arterial pressure reference lines are parallel and appropriately labeled,
wherein a specific area is established to designate optimal blood pressure for data points residing within said specific area,
wherein a plurality of data is segregated and identified as a discrete dataset and displayed as a unique population of graphed data points.

2. The method of claim 1 wherein data points are plotted at graphical intersections of any two of the following parameter magnitude values form a plurality of unique blood pressure measurements: systolic pressure, diastolic pressure, pulse pressure and mean arterial pressure.

3. The method of claim 1 wherein a plurality of datasets are simultaneously displayed and individually identified by different colors, geometric shapes or a combination of color and geometric shape, and displayed accordingly.

4. A computer software product comprising a non-transitory computer-readable medium encoded with code to, when executed by one or more CPUs, to implement the method according to claim 1.

* * * * *